United States Patent [19]

Hoffman

[11] Patent Number: 4,674,486
[45] Date of Patent: Jun. 23, 1987

[54] METHOD OF CORRECTING INGROWN TOENAILS

[76] Inventor: Ronald G. Hoffman, P.O. Box 411, Warsaw, Ky. 41095

[21] Appl. No.: 710,452

[22] Filed: Mar. 11, 1985

[51] Int. Cl.⁴ ............................................. A61F 5/11
[52] U.S. Cl. .................................................. 128/81 A
[58] Field of Search ................... 128/81 R, 81 A, 153; 273/DIG. 7, DIG. 16, DIG. 23; 428/295, 367, 374, 408, 902

[56] References Cited

U.S. PATENT DOCUMENTS

| | | | |
|---|---|---|---|
| 1,596,532 | 8/1926 | Haener | 128/81 A |
| 2,342,530 | 2/1944 | Coates | 128/81 A |
| 2,505,086 | 4/1950 | Andrews | 128/81 A |
| 3,953,641 | 4/1976 | Marquis | 428/295 X |
| 4,057,055 | 11/1977 | Clark | 128/81 A |
| 4,356,228 | 10/1982 | Kobayashi et al. | 428/367 X |

FOREIGN PATENT DOCUMENTS

| | | | |
|---|---|---|---|
| 3233419 | 3/1984 | Fed. Rep. of Germany | 128/81 A |
| 3236804 | 4/1984 | Fed. Rep. of Germany | 128/81 A |
| 50-89695 | 7/1975 | Japan | 428/902 |
| 268681 | 9/1950 | Switzerland | 128/81 A |

*Primary Examiner*—Richard T. Stouffer
*Attorney, Agent, or Firm*—Thorpe, North & Western

[57] ABSTRACT

A method for correcting ingrown toenails includes covering at least a portion of the upper surface of a toenail to be treated with an adhesive, placing a resilient sheet of fibrous reinforced material on the adhesive, where the material is fracturable in a direction crosswise of the direction of growth of the toenail, and bending the lateral edges of the material downwardly to contact and adhere to the side edges of the toenail. When in place, the material urges the side edges of the toenail upwardly to thereby tend to flatten the toenail and eliminate the involution of the edges of the nail.

14 Claims, 5 Drawing Figures

METHOD OF CORRECTING INGROWN TOENAILS

BACKGROUND OF THE INVENTION

The present invention relates to a device and method for reshaping and correcting an ingrown toenail.

Ingrown toenails occur when either one or both of the side edges of the nail become imbedded in the tissue of the toe and produce inflamation. There are a variety of causes of ingrown toenails including improperly designed shoes, high heels, improper trimming of the nails, and deformation of the nails.

A number of devices and methods have been proposed for treating ingrown toenails including those disclosed in U.S. Pat. Nos. 4,057,055, 4,068,656, 3 981.298, 2,505,086, 3,173,416, 3,464,408, 2,405,547, 2,613,667, 3,032,032 and 2,342,530. These patents and other prior art references disclose devices such as metal bands, metal hooks, plastic hooks, and various other appliances for in some fashion treating ingrown toenails. These devices are typically painful to use, ineffective, costly, and difficult to apply and maintain on the toenail.

SUMMARY OF THE INVENTION

It is an object of the invention to provide a method for correcting ingrown toenails in a simple and efficient manner.

It is another object of the invention to provide such a method which may be utilized over an extended period of time without requiring replacement or reapplication.

It is a further object of the invention to provide a method which facilitates correction of an ingrown toenail in a relatively short period of time.

It is an additional object of the invention to provide such a method which can be utilized without professional assistance.

The above and other objects of the invention are realized in a specific illustrative method of correcting ingrown toenails. This method includes covering at least a portion of the upper surface of a toenail to be treated with an adhesive, placing a thin, resilient sheet of material on the adhesive, with the material being fracturable in a direction cross-wise of the direction of growth of the toenail, and then bending the lateral edges of the material downwardly to contact and adhere to the side edges of the toenail. The resiliency of the material urges the side edges of the toenail upwardly as the toenail grows to ultimately effect a cure of the ingrown toenail.

Advantageously, the material which is bonded to the toenail is a thin, flat sheet of essentially unidirectional carbon fiber epoxy composite whose fibers primarily extend cross-wise of the direction of growth of the toenail and whose modulus of elasticity is substantially greater than the modulus of elasticity of the toenail. The carbon fiber epoxy composite may have a thickness of about .005 inches and still achieve the desired corrective effect.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1A:
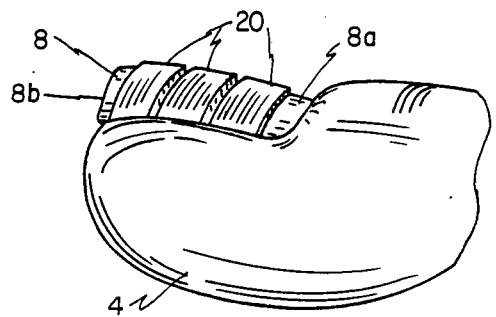
FIG. 1A is a side, fragmented perspective view showing the extremity of a toe with a device for correcting ingrown toenails installed thereon in accordance with the principles of the present invention.
Figure 1B:
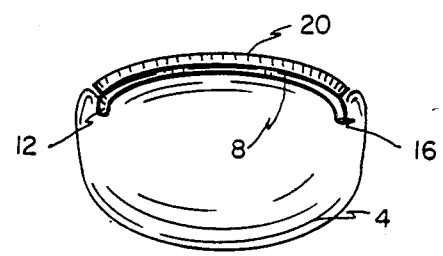
FIG. 1B is an end view of the toe of FIG. 1A, also showing the corrective device.

Referring to FIGS. 1A and 1B, there is shown a toe 4 having an ingrown toenail 8 thereon. FIG. 1B illustrates the nature of an ingrown toenail where edges 12 and 16 of the nail are involuted and imbedded in the flesh of the toe. Such a condition, of course, is quite painful and typically requires minor surgery to temporarily alleviate the condition if it is not otherwise prevented or corrected by way of an appropriate corrective implement.

The present invention involves the placement on the upper surface of the toenail 8 of generally planar, resilient strips of material 20. The material 20 is fracturable in a transverse direction of the direction of growth of the toenail 8 at a plurality of generally linear loci along the direction of growth of the toenail. Advantageously, the strips 20 are composed of a fiberous material such as carbon fiber held together in an epoxy resin, generally known as a carbon fiber epoxy composite. The fibers are unidirectional crosswise or transverse of the direction of growth of the toenail. Exemplary material to make these carbon fiber epoxy composite strips of a thickness of about 0.005 inches can be purchased from Hercules, Inc., with such material known commercially as AS4/3501-SA. This material is readily fracturable or breakable along lines parallel to the fibers, while at the same time providing a high bending modulus of elasticity in the range of about 20 million pounds per square inch (psi).

Although three strips of material 20 are shown in FIG. 1A, a greater or lesser number may be utilized as desired by the party to be treated. If there is a significant curvature of the toenail 8 from the proximal end 8A to the distal end 8B, then a number of strips of material may be needed to enable conforming the strips to the upper surface shape of the toenail.

The strips of material 20 are installed onto the toenail by first applying an adhesive to those portions of the upper surface of the toenail onto which the strips are to be placed A preferred adhesive is cyanoacrylate which cures quite rapidly, within less than 30 seconds. Other adhesives which would be suitable include acrylate, methacrylate, alkyd, cellulostic, epoxy, polyester and vinyl ester. The strips of material are then placed onto the toenail 8, with the side edges of the material bent downwardly to contact and adhere to the side edges of the exposed toenail. The strips should be placed onto the toenail such that the fibers of the material are oriented at about 90 degrees with respect to the growth axis of the nail. The strips of material 20 are sized so as to extend and cover substantially the entire width of the toenail 8. With the strips of material in place the material tends to restore itself to its unflexed planar condition and this produces an upward force on the side edges of the toenail. This force continually operates on the toenail as the toenail grows. Thus, the involution of the edges of the nail is corrected as the nail grows.

Because the strips of material 20 are fracturable in the transverse direction, as the toenail 8 grows, the nail and the material can be easily filed or trimmed with ordinary nail care utensils. Of course, if the nail grows far enough so that it can be clipped at a location between the strips 20, then there is no need to be concerned about cutting the material.

It has been found that the pain associated with this condition is gone and a visible change in curvature of the edges of the toenail will occur within 7 to 8 days after installation of the strips of material, and that an essentially complete cure will occur in about 60 days.

Although the fiberous strips of material 20 were described as being composed of a carbon fiber epoxy composite, any other suitable materials could also be utilized. For example, inorganic materials such as metal wires, fiberglass, boron, or quartz fiber composite and organic polymer composites such as nylon, (polyamide), polypropylene, etc., could also be utilized.

It is important that the material placed on the toenail to exert the straightening force have a high modulus of elasticity. Preferably the modulus of the material should be greater than ten times that of the toenail if the toenail is going to be flattened and corrected within the desired 60 days.

Finally, if biaxial straightening of the toenail (correction of curvature both transversely and axially with the toe) is desired, the material could include fibers which extend axially with the toe interwoven with the transverse fibers.

Figure 2A:
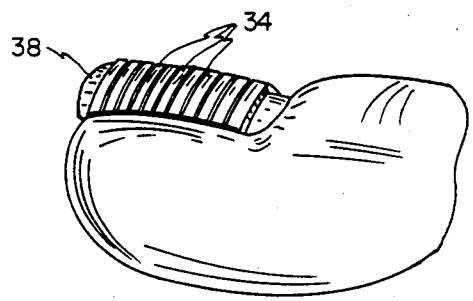
FIG. 2A is a side, fragmented perspective view of an alternative embodiment of the corrective device of the present invention.
Figure 2B:
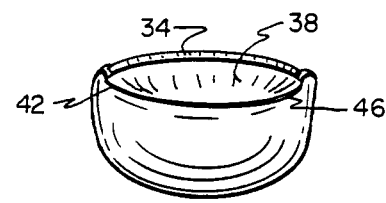
FIG. 2B is an end view of the toe of FIG. 2A, also showing the alternative embodiment.

FIGS. 2A and 2B show an alternative embodiment of a corrective device for application to a toenail. This device includes a series of spring segments 34 overlaid and bonded to the toenail 38 of a toe. The spring segments may be made of stainless steel, or other metallic alloy or resilient material. The spring segments 34, viewed from the side as in FIG. 2B, are in the form of a miniature leaf spring which, before bonding to the toenail, are generally planar.

As with the embodiment described in FIGS. 1A and 1B, the spring segments 34, when bonded to the toenail 38, urge the side eges 42 and 46 (FIG. 2B) upwardly to prevent curling under of the edges. As the toenail 38 grows, the nail can be clipped and at the same time, the forwardmost spring segment removed.

Figure 3:
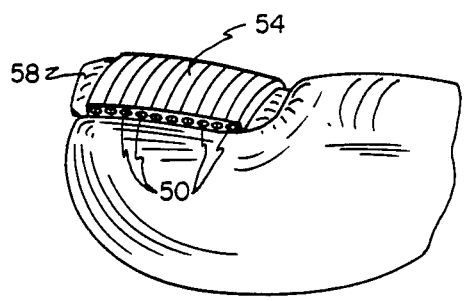
FIG. 3 is a perspective view of still another embodiment of the corrective device of the present invention.

In a final embodiment shown in FIG. 3, generally round, resilient metal wires 50 are held in a generally parallel configuration with an adhesive potting material 54. The resulting element is then placed on and bonded to the nail 58 to be corrected.

In the manner described above, a simple, easy to use and inexpensive device and method are provided for correcting ingrown toenails. The device can be used by an individual without the need of professional care and, because the device is relatively thin and lightweight, there is little discomfort in its use. Since the device is made of a fiberous material or is installed in a series of segments, as the nail grows, the device or portion of the device can be readily removed as the nails are clipped. The device is selected to have a high modulus of elasticity so as to accelerate the corrective process.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A method of correcting ingrown toenails comprising
   providing a resilient sheet of material which is more readily fracturable in a transverse direction than a longitudinal direction, which is generally at right angles to the transverse direction, at a plurality of locations spaced longitudinally along the material, and
   affixing the sheet of material to the upper surface a toenail by bending the side edges of the material downwardly so that the material generally conforms in shape to the upper surface of the toenail, and bonding the material to the toenail so that the transverse direction of the material extends generally across the width of the toenail and urges the side edges of the toenail upwardly.

2. A method as in claim 1 wherein said sheet of material is a carbon fiber epoxy composite material whose fibers extend essentially in the transverse direction.

3. A method as in claim 2 wherein said sheet of material in about 0.005 inches thick.

4. A method as in claim 3 wherein the sheet of material has a modulus of elasticity greater than 20 million psi.

5. A method as in claim 1 wherein said sheet of material is a fiberglass composite matrial whose fibers extend essentially in the transverse direction.

6. A method as in claim 1 wherein said sheet of material comprises a plurality of segments arranged in a series, each of which is breakable from the adjacent segment, and wherein the segments are placed on the nail to extend transversely thereof.

7. A method as in claim 6 wherein said sheet of material is made of stainless steel.

8. A method as in claim 6 wherein said sheet of material is composed of a series of stainless steel wires held in place by potting material.

9. A method as in claim 1 wherein the sheet of material is affixed to the toenail with a cyanoacrylate adhesive.

10. A method as in claim 1 wherein the modulus of elasticity of the sheet of material is selected to be between about 15 and 25 million psi.

11. A method of correcting ingrown toenails comprising
    covering at least a portion of the upper surface of the toenail to be treated with and adhesive,
    placing a resilient sheet of material on the adhesive, said material being more readily fracturable in a cross-wise direction generally at right angles with a length-wide direction which is placed in alignment with the direction of growth of the toenail, and
    bending the lateral edges of the material downwardly to contact and adhere to the side edges of the toenail.

12. A method as in claim 11 wherein the resilient material is selected to have a modulus of elasticity of about 20 million psi.

13. A method as in claim 11 wherein the resilient material is generally planar prior to attachment to a toenail.

14. A method as in claim 11 wherein the resilient material is made of a carbon fiber epoxy composite whose fibers extend cross-wise of the direction of growth of the toenail.

* * * * *